United States Patent [19]

Bourguignon et al.

[11] Patent Number: 4,910,199
[45] Date of Patent: Mar. 20, 1990

[54] IMIDAZO[1,2-B]PYRIDAZINES FOR CORTICAL CHOLINERGIC DEFICIENCIES

[75] Inventors: Jean-Jacques Bourguignon, Hipsheim; Camille G. Wermuth, Strasbourg; Paul Worms, St. Gely Du Fesc, all of France

[73] Assignee: Sanofi, Paris, France

[21] Appl. No.: 238,488

[22] Filed: Aug. 31, 1988

[30] Foreign Application Priority Data

Sep. 1, 1987 [FR] France .................. 87 12167

[51] Int. Cl.$^4$ .............. A61K 31/50; C07D 471/00
[52] U.S. Cl. .................. 514/234.2; 514/248; 544/117
[58] Field of Search ........... 544/236, 117; 514/248, 514/234.2

[56] References Cited

U.S. PATENT DOCUMENTS

| 3,489,755 | 1/1970 | Lombardino | 544/236 |
| 3,828,041 | 8/1974 | Tomcufcik | 544/236 |
| 4,353,903 | 10/1982 | Fabiani | 544/236 |
| 4,464,372 | 8/1984 | Bristol | 544/236 |

Primary Examiner—Donald G. Daus
Attorney, Agent, or Firm—Bacon & Thomas

[57] ABSTRACT

The present invention relates to imidazo[1,2-b]-pyridazines having the formula:

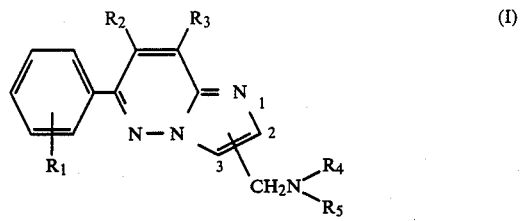

in which: $R_1$ represents hydrogen, a halogen atom, a $C_1$-$C_4$ alkoxy group or a $C_1$-$C_4$ alkyl group occupying one of the free positions of the benzene ring; $R_2$ represents hydrogen, a $C_1$-$C_4$ alkyl group or a phenyl group; $R_3$ denotes hydrogen, a $C_1$-$C_4$ alkyl group or a phenyl group; and $R_4$ and $R_5$ represent hydrogen or a $C_1$-$C_4$ alkyl group, or $R_4$ and $R_5$ form, together with the nitrogen atom to which they are bonded, a 5-membered or 6-membered heterocycle optionally containing a second heteroatom. Application: drugs, especially for the treatment of cortical cholinergic deficiencies.

8 Claims, No Drawings

IMIDAZO[1,2-B]PYRIDAZINES FOR CORTICAL CHOLINERGIC DEFICIENCIES

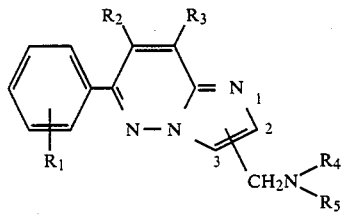

1

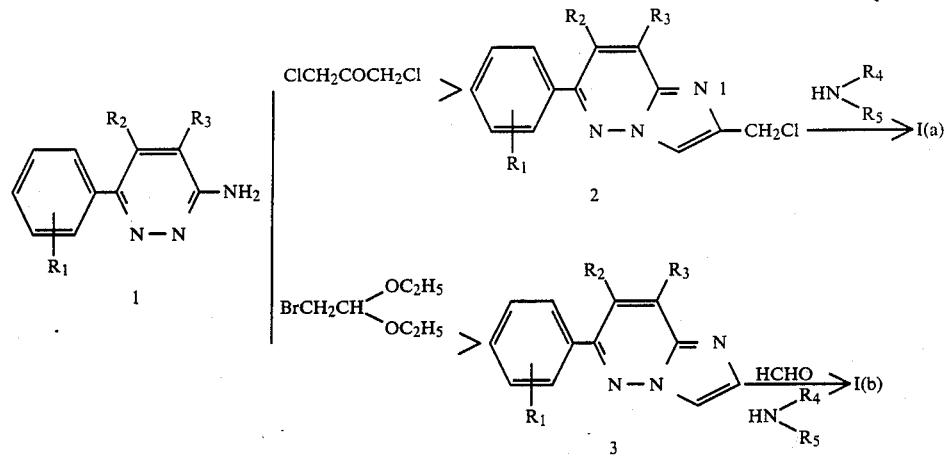

The present invention relates to amino derivatives of imidazo[1,2-b]pyridazine, to a process for their preparation and to pharmaceutical compositions in which the said imidazo[1,2-b]pyridazines are present as active ingredients.

More precisely, according to a first aspect, the present invention therefore relates to novel compounds having the general formula:

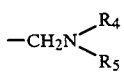

(I)

in which:
$R_1$ represents hydrogen, a halogen atom, a $C_1$-$C_4$ alkoxy group or a $C_1$-$C_4$ alkyl group occupying one of the free positions of the benzene ring;
$R_2$ represents hydrogen, a $C_1$-$C_4$ alkyl group or a phenyl group;
$R_3$ denotes hydrogen, a $C_1$-$C_4$ alkyl group or a phenyl group; and
the group

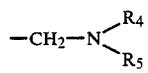

occupies the 2-position or the 3-position of the ring and $R_4$ and $R_5$, taken independently, represent hydrogen or a $C_1$-$C_4$ alkyl group, or else $R_4$ and $R_5$, taken together with the nitrogen atom to which they are bonded, form a 5-membered or 6-membered heterocycle optionally containing a second heteroatom, especially a pyrrolidine, piperidine or morpholine ring,
and to the addition salts formed by the compounds of formula (I) with pharmaceutically acceptable mineral or organic acids.

According to a second aspect, the invention relates to a process for the preparation of the compounds of formula (I), which can be represented by the following scheme:

The compounds of formula (I) are prepared from the appropriately substituted 3-amino-6-phenylpyridazines 1.

If the group

occupies the 2-position (compounds Ia), 1,3-dichloroacetone is reacted with the amine 1 to give the chloromethylated derivative 2. The reaction is carried out by heating the reactants, preferably at between 70° and 110° C., generally for 12 to 15 hours, in an appropriate solvent such as dioxane or acetonitrile, and sodium is added at the end of the reaction.

The compound I(a) is obtained by heating the chloromethylated derivative 2 with the amine $HN\begin{smallmatrix}R_4\\R_5\end{smallmatrix}$ in an inert solvent.

The compound I(a) is salified, if desired, by a method known per se.

If the group

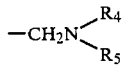

occupies the 3-position (compounds Ib), bromoacetaldehyde is reacted with the amine 1 to give the imidazopyridazine 3. The reaction is carried out in solution in an appropriate solvent, for example a protic solvent such as an alcohol, especially ethanol, or an alcohol/water mixture, at a moderate temperature of between 20° and 50° C.

In practice, the bromoacetaldehyde is prepared by the acid hydrolysis, in an alcoholic medium, of an acetal such as the corresponding diethylacetal, and the resulting alcoholic solution is used directly for the reaction with the amine 1.

The compounds I(b) are obtained from the imidazopyridazine 3 by reaction with formaldehyde solution and the amine

under the conditions of the Mannich reaction.

The resulting products Ib are salified, if desired, by a known method.

The aminopyridazines 1 used as starting materials are known compounds or can be prepared by known processes.

The Examples which follow illustrate the invention without limiting its scope:

EXAMPLE 1

2-Diethylaminomethyl-8-methyl-6-phenylimidazo[1,2-b]pyridazine dihydrochloride (SR 96052 A)

Ia: $R_1=R_2=H$; $R_3=-CH_3$; $R_4=R_5=-C_2H_5$

(A)
2-Chloromethyl-8-methyl-6-phenylimidazo[1,2-b]pyridazine

A solution of 1.85 g of 3-amino-4-methyl-6-phenylpyridazine and 1.52 g of 1,3-dichloroacetone in dioxane is refluxed for 15 hours.

0.41 g of sodium acetate is added and the mixture is refluxed again for 4 hours.

It is evaporated to dryness and the residue is then chromatographed on a silica column. Elution with a 7/3 vol/vol hexane/ethyl acetate mixture gives the expected product, which crystallizes. M.p.: 124° C.; yield: 66%.

(B) SR 96052 A

A solution of 0.65 g of the chloromethylated derivative obtained above and 1.05 ml of diethylamine in 15 ml of tetrahydrofuran is refluxed for 24 hours.

The precipitate of diethylamine hydrochloride is filtered off and washed with a small amount of tetrahydrofuran. The solvent is evaporated off and the residue is taken up in water. Extraction is carried out with ethyl acetate, the organic phase is separated off and the solution is dried.

The solvent is evaporated off and the residue is chromatographed on a silica column. Elution with a 98/2 vol/vol ethyl acetate/methanol mixture to which 2% of aqueous ammonia has been added gives the expected product in the form of an oil. Yield: 52%.

Dihydrochloride

The above base is dissolved in the minimum amount of hot isopropanol and 2.2 equivalents of concentrated hydrochloric acid are added. Crystals separate out on cooling and these are filtered off and washed with isopropyl ether. M.p.: 154° C.

EXAMPLES 2 to 9

(A) Chloromethylated derivatives

The chloromethylated derivatives collated in Table 1 are obtained by following the procedure of Example 1A, but varying the starting amino derivative.

TABLE 1

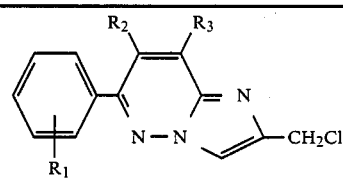

| $R_1$ | $R_2$ | $R_3$ | Physical constants |
|---|---|---|---|
| H | H | H | m.p.: 140° C. |
| H | H | $-C_6H_5$ | chromatographed (1) |
| 3-OCH$_3$ | H | $-CH_3$ | m.p.: 125° C. (1) |
| 4-Cl | H | H | m.p.: 180° C. (1) |
| 2-Cl | H | H | m.p.: 128° C. (1) |

(1) For these products, the reaction was carried out in acetonitrile instead of dioxane.

(B) Starting from the chloromethylated derivatives described in Example 1A and in Table 1, the compounds Ia collated in Table 2 are obtained by following the technique described in Example 1B and varying the amine used.

TABLE 2

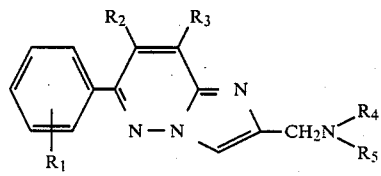

| Ex. no. | SR code no. | $R_1$ | $R_2$ | $R_3$ | $-N\begin{smallmatrix}R_4\\R_5\end{smallmatrix}$ | Base or salt Melting point |
|---|---|---|---|---|---|---|
| 2 | 95775 A | H | H | $-CH_3$ | $-N\bigcirc O$ (morpholino) | base: 112° C. dihydrochloride. 0.5H$_2$O: >260° C. |
| 3 | 96069 A | H | H | H | $-N(C_2H_5)_2$ | dihydrochloride. 1.5H$_2$O: 222° C. |

TABLE 2-continued

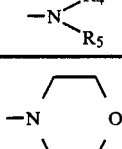

| Ex. no. | SR code no. | R$_1$ | R$_2$ | R$_3$ | $-N\begin{smallmatrix}R_4\\R_5\end{smallmatrix}$ | Base or salt Melting point |
|---|---|---|---|---|---|---|
| 4 | 95842 A | H | H | H | —N⌒O | base: 100° C. dihydrochloride: 240° C. (ethanol) |
| 5 | 96045 A | H | H | —C$_6$H$_5$ | " | dihydrochloride: >300° C. (ethanol) |
| 6 | 96072 A | 3-OCH$_3$ | H | —CH$_3$ | " | dihydrochloride. 1H$_2$O: 217° C. (ethanol) |
| 7 | 96089 A | 4-Cl | H | H | " | monohydrochloride. 0.5H$_2$O: 262° C. (ethanol) |
| 8 | 96095 A | 3-OCH$_3$ | H | —CH$_3$ | —N(C$_2$H$_5$)$_2$ | dihydrochloride. 2H$_2$O |
| 9 | 96110 A | 2-Cl | H | H | —N⌒O | monohydrochloride: 250° C. (ethanol) |

EXAMPLE 10

8-Methyl-3-morpholinomethyl-6-phenylimidazo[1,2-b]pyridazine dihydrochloride (SR 95950 A)

Ib: R$_1$=R$_2$=H; R$_3$=—CH$_3$;

$$-N\begin{smallmatrix}R_4\\R_5\end{smallmatrix} = -N\frown_{\smile}O$$

(A) 8-Methyl-6-phenylimidazo[1,2-b]pyridazine

A mixture of 3 g of bromoacetaldehyde diethylacetal, 0.75 ml of concentrated hydrobromic acid and 0.75 ml of water is refluxed for 2 hours. It is poured into 25 ml of ethanol and neutralized with solid sodium bicarbonate. The precipitate is filtered off and washed with a small amount of ethanol.

1.2 g of 3-amino-4-methyl-6-phenylpyridazine are added to the filtrate (bromoacetaldehyde solution) and the mixture is stirred for 24 hours at room temperature.

It is evaporated to dryness and the residue is taken up with water and rendered alkaline with potassium carbonate. Extraction is carried out with ethyl acetate and the solution is dried over sodium sulfate. The solvent is evaporated off to dryness and the residue is chromatographed on a silica column.

Elution with ethyl acetate gives the expected product. M.p.: 120° C.; yield: 61%.

(B) SR 95950 A

A solution of 0.5 g of the imidazo[1,2-b]pyridazine prepared above, 0.58 ml of a 37% aqueous solution of formaldehyde and 0.416 g of morpholine in methanol is refluxed for 15 hours.

0.58 ml of formaldehyde solution and 0.59 g of morpholine hydrochloride are then added and the mixture is refluxed again for 24 hours. It is evaporated to dryness and the residue is taken up in water.

Extraction is carried out with ethyl acetate, the solution is dried over sodium sulfate and the solvent is evaporated off. The residue crystallizes and is recrystallized from isopropanol. M.p.: 134° C.; yield: 78%.

Dihydrochloride

The base is dissolved in the minimum amount of hot isopropanol and 2.2 equivalents of concentrated hydrochloric acid are added.

After cooling, the crystals are filtered off and washed with isopropyl ether. They are recrystallized from methanol. M.p.: 260° C.

EXAMPLES 11 to 16

(A) The imidazo[1,2-b]pyridazines shown in Table 3 are obtained by following the procedure of Example 10A, but varying the starting aminopyridazine.

TABLE 3

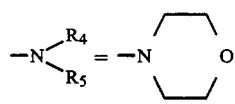

| R$_1$ | R$_2$ | R$_3$ | Melting point or TLC |
|---|---|---|---|
| H | H | H | m.p.: 112° C. |

TABLE 3-continued

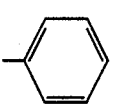

| R₁ | R₂ | R₃ | Melting point or TLC |
|---|---|---|---|
| H | H | (phenyl) | oil - Rf: 0.75 (8/2 ethyl acetate/methanol) |
| 4-Cl | H | H | m.p.: 160° C. |
| 3-OCH₃ | H | CH₃ | (95/5 ethyl acetate/methanol containing 2% of aqueous ammonia) |

Starting from the imidazo[1,2-b]pyridazines described in Example 10A and in Table 3, the compounds Ib collated in Table 4 are obtained by following the technique of Example 10B and varying the amine used.

In the particular case of the derivatives in which $R_4 = R_5 = CH_3$, the reaction can be carried out by heating with dimethylmethyleneammonium iodide (Eschenmoser's salt) in chloroform.

TABLE 4

| Ex. no. | SR code no. | R₁ | R₂ | R₃ | —N⟨R₄/R₅ | Salt or base Melting point |
|---|---|---|---|---|---|---|
| 11 | 96111 A | H | H | —C₆H₅ | —N⟨morpholino⟩ | monohydrochloride. 0.5H₂O, m.p.: 240° C. (ethanol) |
| 12 | 96109 A | 4-Cl | H | H | " | monohydrochloride. 1.5H₂O, m.p.: 230° C. (ethanol) |
| 13 | 96088 A | 3-OCH₃ | H | CH₃ | " | dihydrochloride. 1H₂O, m.p.: 237° C. (methanol) |
| 14 | 96071 A | H | H | CH₃ | —N(CH₃)₂ | dihydrochloride. 1.5H₂O, m.p.: 251° C. |
| 15 | 96070 A | H | H | H | " | base, m.p.: 80° C. dihydrochloride. 3H₂O, m.p.: 234° C. |
| 16 | 96068 A | H | H | H | —N⟨morpholino⟩ | base, m.p.: 114° C. dihydrochloride. 2H₂O, m.p.: 200° C. |

The products according to the invention were studied for their therapeutic action. The interaction of the products according to the invention with muscarinic cholinergic receptors was determined in particular.

There are two subclasses of muscarinic cholinergic receptors in mammals: the $M_1$ and $M_2$ receptors.

The $M_1$-type receptors are concentrated in certain regions of the brain, such as the hippocampus, the cerebral cortex and the striatum, and also in the sympathetic ganglia. These binding sites can be selectively labeled with [³H]-pirenzepine ([³H]-PZ). The $M_2$-type rreceptors predominate in the heart and the ileum and can be labeled with [³H]-N-methylscopolamine ([³H]-NMS). The selectivity of the compounds of the invention with respect to the $M_1$ and $M_2$ sites was determined by studying their in vitro interaction with [³H]-PZ and [³H]-NMS firmly bound with a high affinity to rat hippocampus membranes and smooth guinea-pig ileum muscle, respectively.

METHODOLOGIES (A) Testing for affinity for the $M_1$-type muscarinic cholinergic receptor The interaction of the molecules with the $M_1$-type muscarinic receptors was studied by in vitro measurement, on a rat hippocampus homogenate, of the displacement of tritiated pirenzepine ([³H]-PZ) from its specific binding sites. Aliquots (10 μl) of a 5% (w/v) rat hippocampus homogenate in an Na₂HPO₄ buffer (50 mM, pH 7.40) are incubated for 2 h at 4° C. in the presence of [³H]-PZ (76 Ci/nmol; final concentration 1 nM) and increasing concentrations of the test product. The final volume is 2 ml. The reaction is stopped by centrifugation for 10 min at 50 000×g. After decantation and washing of the residues, the bound radio-activity is counted by liquid scintillation. The non-specific binding is determined in the presence of 10 μM atropine sulfate. The 50% inhibitory concentration (IC$_{50}$) is determined graphically. (Ref.: J. D. Watson, W. R. Roeskoe and H. I. Yamamura, Life Sci., 31, 2019–2029, 1982).

(B) Testing for affinity for the M$_2$-type muscarinic cholinergic receptor

The interaction with the M$_2$-type muscarinic receptors was studied by in vitro measurement, on a smooth guinea-pig ileum muscle homogenate, of the displacement of tritiated N-methylscopolamine ([$^3$H]-NMS) from its specific binding sites. Aliquots (50 μl) of a 0.625% (w/v) smooth guinea-pig ileum muscle homogenate in HEPES buffer (20 mM) containing NaCl (100 mM) and MgCl$_2$ (10 mM) (final pH: 7.5) are incubated for 20 min at 30° C. in the presence of [$^3$H]-NMS (85 Ci/nmol; final concentration 0.3 nM) and increasing concentrations of the test products. The final volume is 1 ml. The reaction is topped by centrifugation for 5 min at 15 000×g. The non-specific binding is determined in the presence of 10 μM atropine sulfate. (Ref.: R. Hammer, C. P. Berrie, N. I. M. Birdsall, A. S. V. Burgen and E. C. Hulme, Nature, 283, 90–92, 1980; E. C. Hulme, N. I. M. Birdsall, A. S. V. Burgen and P. Mettha, Mol. Pharmacol., 14, 737–750, 1978.)

(C) RESULTS

Table 5 indicates the affinities of the products of the invention for the M$_1$ and M$_2$ receptors. The results are expressed as 50 percent inhibitory concentrations (IC$_{50}$), i.e. the concentration (in μM) which induces the displacement of 50% of the tritiated ligand bound to the membrane receptors. The IC$_{50}$ for $^3$H-pirenzepine displacement represents the affinity for the M$_1$ receptor; The IC$_{50}$ for $^3$H-NMS displacement represents the affinity for the M$_2$ receptor.

Also, the 3rd column indicates the ratio r of the IC$_{50}$ values for M$_1$ and M$_2$, which expresses the selectivity of the products with respect to one of the receptor types.

TABLE 5

| Product no. | $^3$H-Pirenzepine (M$_1$) IC$_{50}$ μM | $^3$H-NMS (M$_2$) IC$_{50}$ μM | r = (M$_2$/M$_1$) |
| --- | --- | --- | --- |
| SR 95950 A | 1.4 | >100 | >71 |
| SR 96052 A | 0.5 | 65 | 130 |
| SR 96069 A | 1.5 | 100 | 66 |
| SR 96088 A | 8 | n.d. | — |
| SR 96089 A | 3 | >100 | >33 |
| SR 96095 A | 0.4 | 65 | 162 | n.d.: not determined

These results show that the compounds according to the invention have a strong affinity for muscarinic cholinergic receptors, with a marked specificity for the M$_1$-type central receptors.

Furthermore, some of the compounds according to the invention were subjected to an in vivo pharmacological study.

IN VIVO PHARMACOLOGICAL STUDY

Pirenzepine (PZ) is a specific antagonist of the M$_1$ central muscarinic cholinergic receptors. The intrastriatal injection of PZ into mice induces rotatory behavior. The antagonism of this behavior by the products according to the invention was studied.

The products according to the invention are injected intraperitoneally (i.p.) after solubilization in distilled water or suspension in a 5% solution of gum arabic. The control animals receive an injection of the pure solvent under the ssame conditions.

The animals used are female mice (Swiss, CD 1, Charles River, France) with a body weight of between 25 and 30 grams.

The pirenzepine is dissolved in a phosphate buffer and the pH of the solution is 6.

The test products of their solvents are injected intraperitoneally in a volume of 0.4 ml per 20 g of body weight, 15 minutes before a direct injection of pirenzepine into the right striatum of the mouse at a dose of 1 μg in 1 μl of solvent, according to the method described by P. WORMS et al. in Eur. J. Pharmacol., 1986, 121, 395–401.

The number of contralateral rotations (rotations in the opposite direction to the side injected) was counted for three 2-minute periods after injection of the pirenzepine: 2nd to 4th, 8th to 10th and 13th to 15th minutes. Each treatment consists of 3 to 4 doses with 10 animals per dose. The total number of rotations and the percentage antagonism with respect to the control group are calculated for each treatment.

The 50% effective dose (ED$_{50}$), i.e. the dose which causes a 50% reduction in the number of rotations induced by pirenzepine, is determined graphically for each product. The results are reported in Table 6.

TABLE 6

| Product no. | Pirenzepine antagonism ED$_{50}$ mg/kg i.p. |
| --- | --- |
| SR 95842 A | 3 |
| SR 95950 A | 5 |
| SR 96052 A | 8 |
| SR 96068 A | 10 |
| SR 96070 A | 3 |
| SR 96095 A | 5 |
| SR 96109 A | 8 |
| SR 96111 A | 7 |

Furthermore, tests carried out on some of the compounds according to the invention showed that the compounds (I) pass through the blood-brain and digestive barriers.

Finally, the compounds according to the invention showed no signs of apparent toxicity in the doses at which they are active.

Consequently, the compounds (I) can be used as drugs, especially in cases where a cortical cholinergic deficiency is evident and in particular in the case of dementia of the Alzheimer type.

According to another aspect, the present application therefore relates to the pharmaceutical compositions which contain at least one of the compounds of formula (I) or one of their salts as the active ingredient.

In the pharmaceutical compositions of the present invention for oral, sublingual, subcutaneous, intramuscular, intravenous, percutaneous or rectal administration, the active ingredients of formula I above can be administered to humans in single dosage forms, mixed with conventional pharmaceutical excipients, especially for the treatment of senile dementia. The appropriate single dosage forms include oral dosage forms, such as tablets, gelatin capsules, powders, granules and solutions or suspensions to be taken orally, sublingual and buccal dosage forms, subcutaneous, intramuscular or intravenous dosage forms and rectal dosage forms.

To achieve the desired effect, the dose of active principle can vary between 50 and 2000 mg per day.

Each unit dose can contain from 10 to 500 mg of active ingredient combined with a pharmaceutical excipient. This unit dose can be administered 1 to 4 times per day.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other appropriate substances, or else they can be treated so as to have a sustained or delayed activity and continuously release a predetermined amount of active principle.

A preparation in the form of gelatin capsules is obtained by mixing the active ingredient with a diluent and pouring the resulting mixture into soft or hard gelatin capsules.

Water-dispersible granules or powders can contain the active ingredient mixed with dispersants or wetting agents, or suspending agents such as polyvinylpyrrolidone, and with sweeteners or taste correctors.

For rectal administration, suppositories are used; these are prepared with binders which melt at the temperature of the rectum, for example cacao butter or polyethylene glycols.

For parenteral administration, aqueous suspensions, isotonic salt solutions or injectable sterile solutions are used; these contain pharmacologically compatible dispersants and/or wetting agents, for example propylene glycol or butylene glycol.

The active principle can also be formulated as microcapsules, together with one or more excipients or additives if appropriate.

Thus, by way of example, it is possible to prepare gelatin capsules based on one of the compounds of Examples 1 to 16 and having the following composition:
active principle: 25 mg
lactose: 110 mg
magnesium stearate: 5 mg
by intimately mixing the above ingredients and pouring the mixture into hard gelatin capsules.

What is claimed is:

1. Imidazo[1,2-b]pyridazines of the formula:

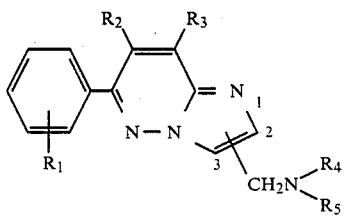

in which:

$R_1$ represents hydrogen, a halogen atom, a $C_1$-$C_4$ alkoxy group or a $C_1$-$C_4$ alkyl group occupying one of the free positions of the benzene ring;

$R_2$ represents hydrogen, a $C_1$-$C_4$ alkyl group or a phenyl group;

$R_3$ represents hydrogen, a $C_1$-$C_4$ alkyl group or a phenyl group; and the group

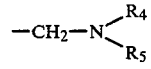

occupies the 2-position or 3-position of the ring and, in this group, $R_4$ and $R_5$, taken independently, represent hydrogen or a $C_1$-$C_4$ alkyl group, or $R_4$ and $R_5$, taken with the nitrogen atom to which they are bonded, form a 5-membered or 6-membered heterocycle, optionally having a second heteroatom, selected from pyrrolidine, piperidine or morpholine, and their salts with pharmaceutically acceptable mineral or organic acids.

2. Compounds according to claim 1 in which the group

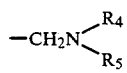

occupies the 2-position of the imidazole ring and in which $R_1$, $R_2$, $R_3$, $R_4$ and $R_5$ are as defined in claim 1.

3. Compounds according to claim 1 in which the group

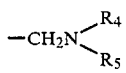

occupies the 3-position of the imidazole ring and in which $R_1$, $R_2$, $R_3$, $R_4$ and $R_5$ are as defined in claim 1.

4. A pharmaceutical composition for use in the treatment of cortical cholinergic deficiencies in humans comprising a pharmaceutically effective amount of a compound of formula (I) as active principle in combination with a pharmaceutically acceptable carrier or excipient.

5. A pharmaceutical composition as claimed in claim 4, wherein the active principle is present in dosage unit form.

6. A pharmaceutical composition as claimed in claim 5, wherein the unit dosage is between 10 mg and 500 mg of active ingredient.

7. A pharmaceutical composition as claimed in claim 6, wherein the unit dose can be administered 1 to 4 times per day.

8. A pharmaceutical composition as claimed in claim 4, wherein the cortical cholingeric deficiency is Alzheimer-type dementia.

* * * * *